(12) United States Patent
Petkus et al.

(10) Patent No.: US 11,663,415 B2
(45) Date of Patent: May 30, 2023

(54) SYSTEMS AND METHODS FOR VOICE ASSISTED HEALTHCARE

(71) Applicant: WALGREEN CO., Deerfield, IL (US)

(72) Inventors: Julija Alegra Petkus, Oak Park, IL (US); Andrew David Schweinfurth, Chicago, IL (US); Stephen Elijah Zambo, Lake Villa, IL (US)

(73) Assignee: WALGREEN CO., Deerfield, IL (US)

( * ) Notice: Subject to any disclaimer, the term of this patent is extended or adjusted under 35 U.S.C. 154(b) by 325 days.

(21) Appl. No.: 17/008,531

(22) Filed: Aug. 31, 2020

(65) Prior Publication Data

US 2022/0067293 A1    Mar. 3, 2022

(51) Int. Cl.
  *G06F 40/30* (2020.01)
  *G10L 15/22* (2006.01)
  *G16H 20/10* (2018.01)

(52) U.S. Cl.
  CPC .............. *G06F 40/30* (2020.01); *G10L 15/22* (2013.01); *G16H 20/10* (2018.01)

(58) Field of Classification Search
  CPC ... G06F 40/30; G10L 15/22; G10L 2015/223; G16H 20/10
  See application file for complete search history.

(56) References Cited

U.S. PATENT DOCUMENTS

| | | | |
|---|---|---|---|
| 10,277,743 B1 * | 4/2019 | Agarwal | G06F 40/216 |
| 10,532,885 B1 | 1/2020 | Brady et al. | |
| 10,838,954 B1 | 11/2020 | Santos et al. | |
| 2009/0037474 A1 * | 2/2009 | Faulkner | G16H 40/67 |
| 2014/0032223 A1 * | 1/2014 | Powe | G16H 40/63 |
| | | | 704/E11.001 |
| 2014/0222436 A1 * | 8/2014 | Binder | G06F 3/167 |
| | | | 704/275 |
| 2016/0307449 A1 | 10/2016 | Gordon et al. | |
| 2017/0330215 A1 | 11/2017 | Bruno et al. | |
| 2018/0067991 A1 | 3/2018 | Agarwal et al. | |
| 2018/0253209 A1 * | 9/2018 | Jaygarl | G06F 9/451 |
| 2018/0314552 A1 * | 11/2018 | Kim | G06F 9/485 |
| 2018/0330723 A1 * | 11/2018 | Acero | G06F 3/16 |
| 2018/0341643 A1 * | 11/2018 | Alders | G10L 15/1822 |
| 2019/0205468 A1 | 7/2019 | Barnes, Jr. | |
| 2019/0251959 A1 * | 8/2019 | Engles | H04M 3/523 |
| 2019/0272921 A1 * | 9/2019 | Koll | G10L 15/26 |
| 2020/0075016 A1 | 3/2020 | Goldstein et al. | |

(Continued)

OTHER PUBLICATIONS

Vega et al., Towards a multi-screen interactive ad delivery platform, IEEE, 10 pp. (2017).

(Continued)

*Primary Examiner* — Eric Yen
(74) *Attorney, Agent, or Firm* — Marshall, Gerstein & Borun LLP; Randall G. Rueth

(57) ABSTRACT

The following relates generally to voice assisted healthcare. In some embodiments, a digital assistant receives audio data, and determines an intent from the audio data. The digital assistant may then match the determined intent to a flow of a set of flows, where the set of flows may include at least one of: (i) submitting a prescription, (ii) refilling a prescription, (iii) changing a pickup location, (iv) requesting a status update for a prescription, or (v) initiating a pharmacy chat session. The matched flow of the set of flows may then be executed.

19 Claims, 4 Drawing Sheets

(56) References Cited

U.S. PATENT DOCUMENTS

| | | |
|---|---|---|
| 2020/0312315 A1 | 10/2020 | Li et al. |
| 2020/0320365 A1* | 10/2020 | Arat .......................... G06F 8/38 |
| 2021/0065017 A1* | 3/2021 | Ramnani ................. G06N 5/04 |
| 2021/0327572 A1* | 10/2021 | Sadhvani ................. G06N 3/08 |
| 2022/0012018 A1* | 1/2022 | Trim ....................... G06N 5/04 |
| 2022/0157315 A1* | 5/2022 | Raux .................. G10L 15/1822 |

OTHER PUBLICATIONS

European Patent Application No. 21193878.2, Extended European Search Report, dated Jan. 5, 2022.
European Patent Application No. 21193880.8, Extended European Search Report, dated Jan. 28, 2022.

* cited by examiner

SYSTEMS AND METHODS FOR VOICE ASSISTED HEALTHCARE

BACKGROUND

Many modern healthcare systems are accessed through use of a smartphone, tablet, personal computer, or other computing device. However, in some situations, access to the healthcare related systems though these devices may be cumbersome. For example, a user may wish to fill a prescription, but does not have easy access to her smartphone (e.g., the user is driving in a car and would like to keep both hands on the steering wheel, or the smartphone is misplaced, etc.). In another example, the user may have access to a smartphone, but it is difficult for the user to use the smartphone because of a physical or medical condition (e.g., the user has broken his wrists, making typing on the smartphone difficult).

The systems and methods disclosed herein provide solutions to these problems and others.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one aspect, there is a computer computer-implemented method for voice assisted healthcare. The method may comprise determining an intent from digital data, wherein the digital data comprises audio data or text message data. The method may further comprise matching the determined intent to a flow of a set of flows, wherein the set of flows includes at least one of: (i) submitting a prescription, (ii) refilling a prescription, (iii) changing a pickup location, (iv) requesting a status update for a prescription, or (v) initiating a pharmacy chat session. The method may still further comprise executing the matched flow of the set of flows.

In another aspect, there is a computer computer-implemented method for voice assisted healthcare. The method may comprise determining an intent from digital data, wherein the digital data comprises audio data or text message data. The method may further comprise matching the determined intent to a flow of a set of flows, wherein the set of flows includes locating at least one of: (i) a doctor's office, (ii) an online medical care provider, (iii) a site providing virus testing, (iv) a site administering a vaccine, (v) a provider of mental healthcare, (vi) a vision care provider, (vii) a hearing care provider, or (viii) a physical therapist. The method may still further comprise executing the matched flow of the set of flows.

In yet another aspect, there is a computer system for voice assisted healthcare. The computer system may include one or more processors configured to determine an intent from audio data. The one or more processors may be further configured to match the determined intent to a flow of a set of flows, wherein the set of flows includes at least one of: (i) submitting a prescription, (ii) refilling a prescription, (iii) changing a pickup location, (iv) requesting a status update for a prescription, or (v) initiating a pharmacy chat session. The one or more processors may be further configured to execute the matched flow of the set of flows.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

DETAILED DESCRIPTION

The present embodiments relate to, inter alia, voice assisted healthcare. In this regard, one objective of the present application is to provide better or easier access to healthcare. For instance, a user may be in a situation where it is difficult for the user to type into her smartphone, and so may prefer to access the healthcare via voice assistance. Alternatively, even if the user is not in a situation where it is particularly difficult to type into a device, the user may still prefer to access the healthcare via voice techniques for convenience or personal preference. To this end, some embodiments enable a simple plug and play platform that provides easy access to healthcare.

Exemplary Infrastructure

Figure 1:
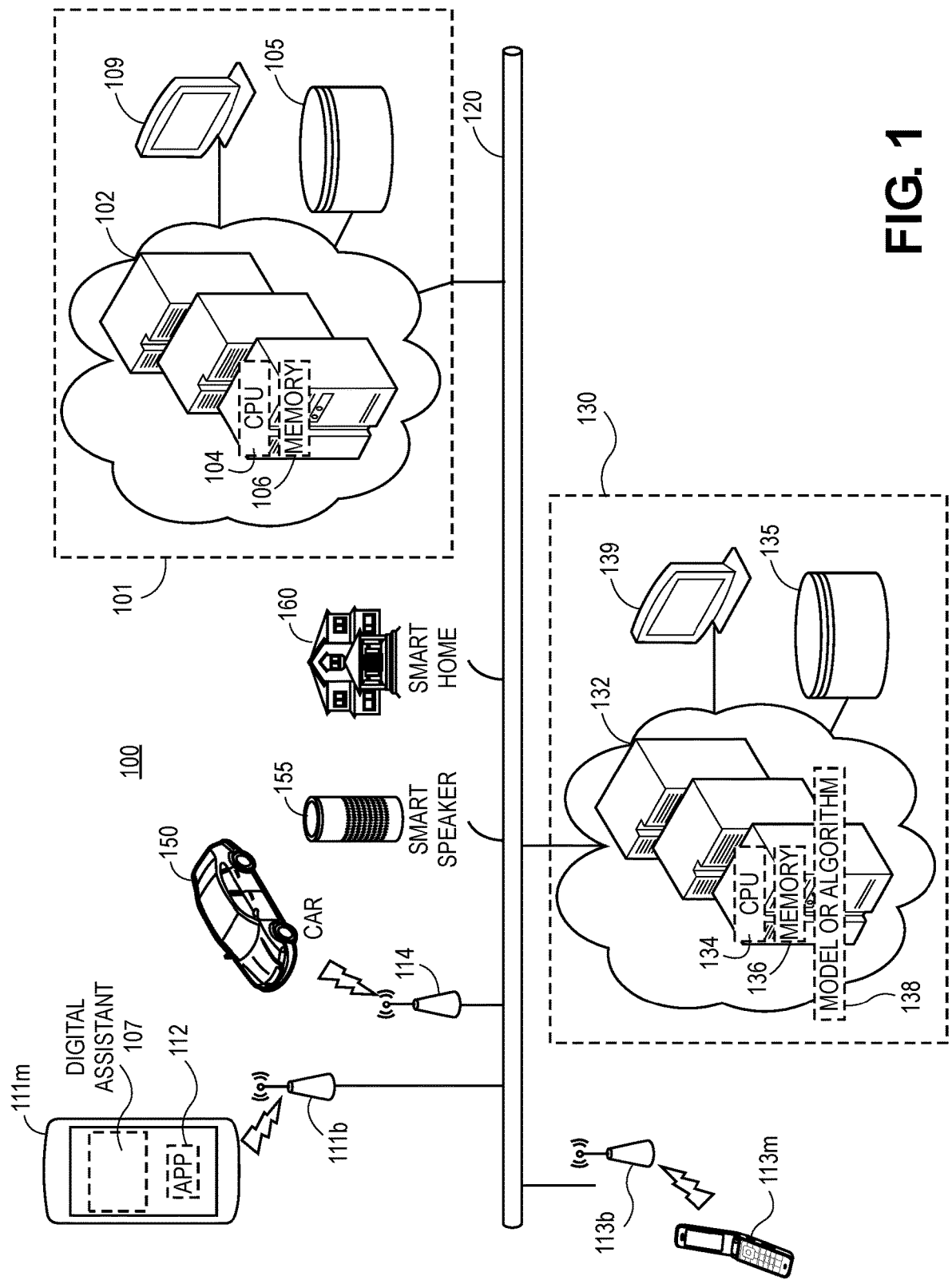
FIG. 1 illustrates a platform 100 configured for voice assisted healthcare in accordance with various embodiments disclosed herein.

FIG. 1 illustrates a platform 100 configured for voice assisted healthcare in accordance with various embodiments disclosed herein. In the example embodiment of FIG. 1, the platform 100 includes healthcare provider 101 (e.g., a first entity). The healthcare provider 101 may be any healthcare providing entity, such as a pharmacy, hospital, doctor's office, lab, clinic, urgent care facility, and so forth. In the example of FIG. 1, healthcare provider 101 includes server(s) 102, which may comprise one or more computer servers. In various embodiments, server(s) 102 comprise multiple servers, which may comprise multiple, redundant, or replicated servers as part of a server farm. In still further embodiments, server(s) 102 are implemented as cloud-based servers. For example, server(s) 102 may comprise a cloud-based platform such as MICROSOFT AZURE, AMAZON AWS, or the like.

Server(s) 102 may include one or more processor(s) 104 as well as one or more computer memories 106. The memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memories 106 may store an operating system (OS) (e.g., Microsoft Windows, Linux, Unix, etc.) capable of facilitating the functionalities, apps, methods, or other software as discussed herein. The memories 106 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, a machine learning component. It should be appreciated that one or more other applications may be envisioned and that are executed by the processor(s) 104.

The processor(s) 104 may be connected to the memories 106 via a computer bus responsible for transmitting electronic data, data packets, or otherwise electronic signals to and from the processor(s) 104 and memories 106 in order to implement or perform the machine readable instructions, methods, processes, elements or limitations, as illustrated, depicted, or described for the various flowcharts, illustrations, diagrams, figures, and/or other disclosure herein.

The processor(s) 104 may interface with the memory 106 via the computer bus to execute the operating system (OS). The processor(s) 104 may also interface with the memory 106 via the computer bus to create, read, update, delete, or otherwise access or interact with the data stored in the memories 106 and/or the database 105 (e.g., a relational database, such as Oracle, DB2, MySQL, or a NoSQL based database, such as MongoDB). The data stored in the memories 106 and/or the database 105 may include all or part of any of the data or information described herein, including, for example, the one or more search requests, the one or more transaction details, and the profile information of the user.

The server(s) 102 may further include a communication component configured to communicate (e.g., send and receive) data via one or more external/network port(s) to one or more networks or local terminals, such as computer network 120 and/or terminal 109 (for rendering or visualizing) as described herein. In some embodiments, server(s) 102 may include a client-server platform technology such as ASP.NET, Java J2EE, Ruby on Rails, Node.js, a web service or online API, responsive for receiving and responding to electronic requests. The server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein. According to some embodiments, the server(s) 102 may include, or interact with, one or more transceivers (e.g., WWAN, WLAN, and/or WPAN transceivers) functioning in accordance with IEEE standards, 3GPP standards, 4G standards, 5G standards or other standards, and that may be used in receipt and transmission of data via external/network ports connected to computer network 120.

Server(s) 102 may further include or implement an operator interface configured to present information to an administrator or operator and/or receive inputs from the administrator or operator. As shown in FIG. 1, an operator interface may provide a display screen (e.g., via terminal 109). Server(s) 102 may also provide I/O components (e.g., ports, capacitive or resistive touch sensitive input panels, keys, buttons, lights, LEDs), which may be directly accessible via or attached to server(s) 102 or may be indirectly accessible via or attached to terminal 109. According to some embodiments, an administrator or operator may access the server(s) 102 via terminal 109 to review information, make changes, input training data, and/or perform other functions.

As described above herein, in some embodiments, server(s) 102 may perform the functionalities as discussed herein as part of a "cloud" network or may otherwise communicate with other hardware or software components within the cloud to send, retrieve, or otherwise analyze data or information described herein. Furthermore, server(s) 102 and/or their respective memorie(s) 106 are configured to store data including for example, patient data, pharmacy data, prescription data, and so forth.

In general, a computer program or computer based product, or application, in accordance with some embodiments may include a computer usable storage medium, or tangible, non-transitory computer-readable medium (e.g., standard random access memory (RAM), an optical disc, a universal serial bus (USB) drive, or the like) having computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C #, Objective-C, Java, Scala, Actionscript, Javascript, HTML, CSS, XML, etc.).

The example of FIG. 1 further illustrates audio analyzing entity 130 (e.g., a second entity). The audio analyzing entity 130 may be any entity capable of analyzing digital data, such as audio data or text message data. In some embodiments, the healthcare provider 101 is a physically separate entity than the audio analyzing entity 130 (e.g., the healthcare provider 101 and the audio analyzing entity 130 are of different companies and are located in different geographic locations). Moreover, by separating the healthcare provider 101 and the audio analyzing entity 130, data security and data privacy may be improved. For example, as will be explained below, the audio analyzing entity 130 may receive audio data from mobile device 111m; and, rather than send the entire audio data to the healthcare provider 101, the audio analyzer 130 may send only an intent determined from the audio data to the healthcare provider. Although the example of FIG. 1 is illustrated with respect to audio data, it should be understood that any digital data, such as text message data, may be used in addition to or in place of the audio data.

In the example of FIG. 1, audio analyzing entity 130 includes server(s) 132, which may comprise one or more computer servers. In various embodiments, server(s) 132 comprise multiple servers, which may comprise multiple, redundant, or replicated servers as part of a server farm. In still further embodiments, server(s) 132 are implemented as cloud-based servers. For example, server(s) 132 may comprise a cloud-based platform such as MICROSOFT AZURE, AMAZON AWS, or the like.

Server(s) 132 may include one or more processor(s) 134 as well as one or more computer memories 136. The memories 136 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memories 136 may store an operating system (OS) (e.g., Microsoft Windows, Linux, Unix, etc.)

capable of facilitating the functionalities, apps, methods, or other software as discussed herein. The memories 136 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, a machine learning component. It should be appreciated that one or more other applications may be envisioned and that are executed by the processor(s) 134.

The processor(s) 134 may be connected to the memories 136 via a computer bus responsible for transmitting electronic data, data packets, or otherwise electronic signals to and from the processor(s) 134 and memories 136 in order to implement or perform the machine readable instructions, methods, processes, elements or limitations, as illustrated, depicted, or described for the various flowcharts, illustrations, diagrams, figures, and/or other disclosure herein.

The processor(s) 134 may interface with the memory 136 via the computer bus to execute the operating system (OS). The processor(s) 134 may also interface with the memory 136 via the computer bus to create, read, update, delete, or otherwise access or interact with the data stored in the memories 136 and/or the database 135 (e.g., a relational database, such as Oracle, DB2, MySQL, or a NoSQL based database, such as MongoDB). The data stored in the memories 136 and/or the database 135 may include all or part of any of the data or information described herein, including, for example, the one or more search requests, the one or more transaction details, and the profile information of the user.

The server(s) 132 may further include a communication component configured to communicate (e.g., send and receive) data via one or more external/network port(s) to one or more networks or local terminals, such as computer network 120 and/or terminal 139 (for rendering or visualizing) as described herein. In some embodiments, server(s) 132 may include a client-server platform technology such as ASP.NET, Java J2EE, Ruby on Rails, Node.js, a web service or online API, responsive for receiving and responding to electronic requests. The server(s) 132 may implement the client-server platform technology that may interact, via the computer bus, with the memories(s) 136 (including the applications(s), component(s), API(s), data, etc. stored therein) and/or database 135 to implement or perform the machine readable instructions, methods, processes, elements or limitations, as illustrated, depicted, or described for the various flowcharts, illustrations, diagrams, figures, and/or other disclosure herein. According to some embodiments, the server(s) 132 may include, or interact with, one or more transceivers (e.g., WWAN, WLAN, and/or WPAN transceivers) functioning in accordance with IEEE standards, 3GPP standards, 4G standards, 5G standards or other standards, and that may be used in receipt and transmission of data via external/network ports connected to computer network 120.

Server(s) 132 may further include or implement an operator interface configured to present information to an administrator or operator and/or receive inputs from the administrator or operator. As shown in FIG. 1, an operator interface may provide a display screen (e.g., via terminal 139). Server(s) 132 may also provide I/O components (e.g., ports, capacitive or resistive touch sensitive input panels, keys, buttons, lights, LEDs), which may be directly accessible via or attached to server(s) 132 or may be indirectly accessible via or attached to terminal 139. According to some embodiments, an administrator or operator may access the server(s) 132 via terminal 139 to review information, make changes, input training data, and/or perform other functions.

As described above herein, in some embodiments, server(s) 132 may perform the functionalities as discussed herein as part of a "cloud" network or may otherwise communicate with other hardware or software components within the cloud to send, retrieve, or otherwise analyze data or information described herein. Furthermore, server(s) 132 and/or their respective memorie(s) 136 are configured to store data.

In general, a computer program or computer based product, or application, in accordance with some embodiments may include a computer usable storage medium, or tangible, non-transitory computer-readable medium (e.g., standard random access memory (RAM), an optical disc, a universal serial bus (USB) drive, or the like) having computer-readable program code or computer instructions embodied therein, wherein the computer-readable program code or computer instructions may be installed on or otherwise adapted to be executed by the processor(s) 134 (e.g., working in connection with the respective operating system in memories 136) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C #, Objective-C, Java, Scala, Actionscript, Javascript, HTML, CSS, XML, etc.).

In the example embodiment of FIG. 1, the healthcare provider 101 and audio analyzing entity 130 are communicatively connected, via computer network 120 and base stations 111*b* and 113*b* to respective mobile devices 111*m* and 113*m*. The healthcare provider 101 and audio analyzing entity 130 are further communicatively connected, via computer network 120 and base station 114 to car 150. The healthcare provider 101 and audio analyzing entity 130 are still further communicatively connected, via computer network 120 to smart speaker 155 and smart home 160. Computer network 120 may comprise a packet based network operable to transmit computer data packets among the various devices and servers described herein. For example, computer network 120 may consist of any one or more of Ethernet based network, a private network, a local area network (LAN), and/or a wide area network (WAN), such as the Internet. In addition, in some embodiments, computer network 120 may comprise cellular or mobile networks to facilitate data packet traffic (e.g., mobile device movement data) to and from base stations 111*b* and/or 113*b*. Base stations 111*b* and 113*b* may comprise cellular towers or access points implementing any one or more cellular or mobile device standards, including, for example, any of GSM, UMTS, CDMA, NMT, LTE, 5G NR, or the like.

Exemplary Embodiments

The following discussion teaches systems and methods for, inter alia, voice assisted healthcare. For example, the following discussion teaches how to leverage the example infrastructure of FIG. 1 to provide better healthcare to a patient.

Figure 2:
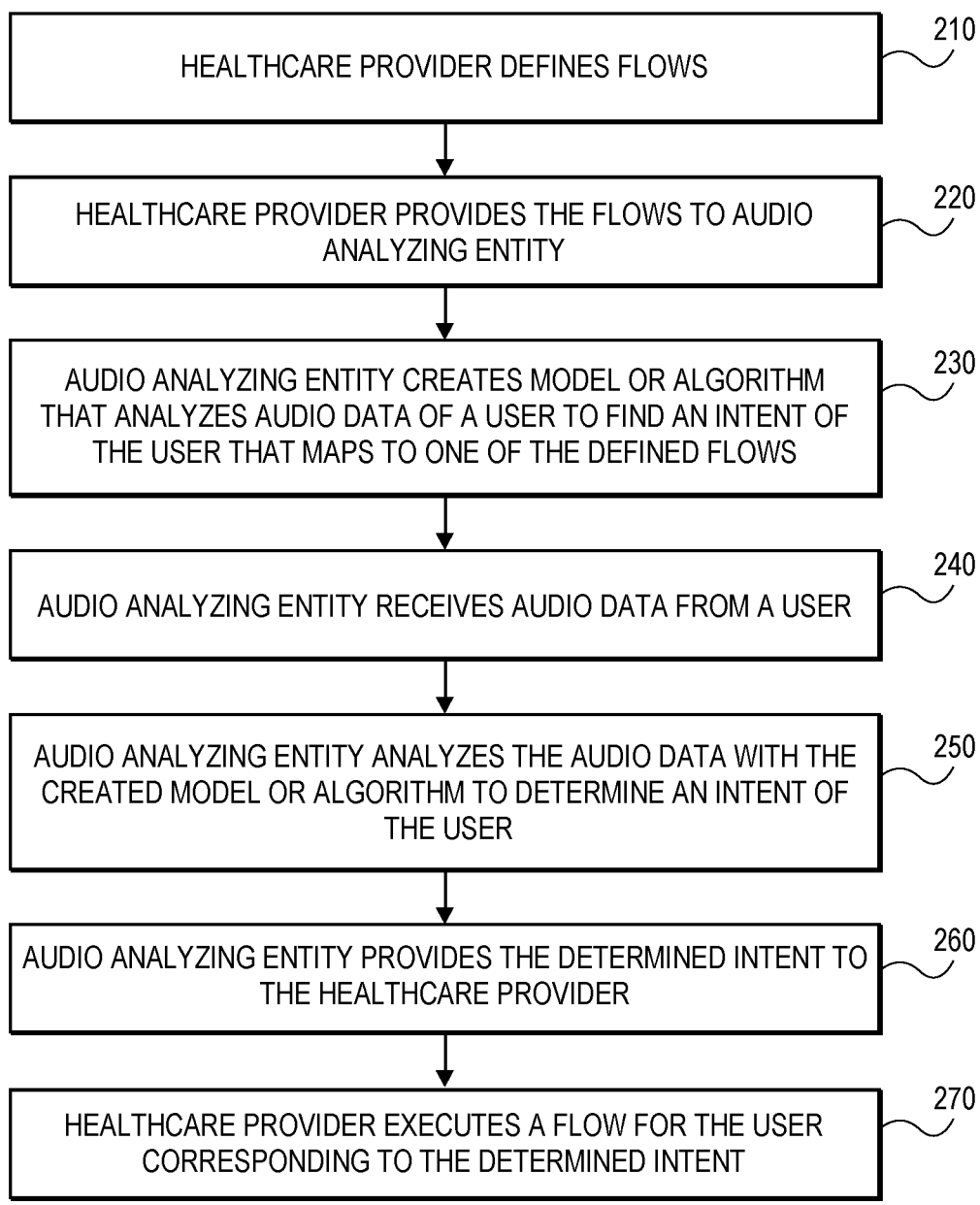
FIG. 2 shows an overview flowchart of an example implementation.

FIG. 2 shows an overview flowchart of an example implementation. With reference thereto, at step 210, the healthcare provider 101 defines a set of flows. The flows may be flow processes of an app or website. For example, if the healthcare provider 101 is a pharmacy, the flows may be, inter alia: (i) submitting a prescription, (ii) refilling a prescription, (iii) changing a pickup location, (iv) requesting a status update for a prescription, or (v) initiating a pharmacy chat session.

In another example, if the healthcare provider is a healthcare finder (e.g., an online service that locates healthcare providers), the flows may be, inter alia, locating: (i) a doctor's office, (ii) an online medical care provider, (iii) a site providing virus testing, such as Corona virus testing, (iv) a site administering a vaccine, such as administering a Corona virus vaccine, (v) a provider of mental healthcare, (vi) a vision care provider, (vii) a hearing care provider or (viii) a physical therapist.

At step 220, the healthcare provider 101 provides the flows to audio analyzing entity 130. At step 230, the audio analyzing entity 130 creates model or algorithm 138 that analyzes audio data of a user to find an intent of the user that maps to one of the defined flows. In some embodiments, the model or algorithm 138 may be provided to a computing device so that it may be run as part of the digital assistant 107 to find an intent based on audio data.

At step 240, the audio analyzing entity 130 receives audio data from a user. The user may send the audio data from any device including a smartphone, tablet, personal computer, car, smart home, smart speaker, or so forth. At step 250, audio analyzing entity 130 analyzes the audio data with the created model or algorithm (e.g., model 138 of FIG. 1) to determine an intent of the user. At step 260, the audio analyzing entity 130 provides the determined intent to the healthcare provider 101. At step 270, the healthcare provider 101 executes a flow for the user corresponding to the determined intent.

Furthermore, although the example of FIG. 2 is illustrated with respect to audio data, it should be understood that any digital data, such as text message data, may be used in addition to or in place of the audio data.

Figure 3:
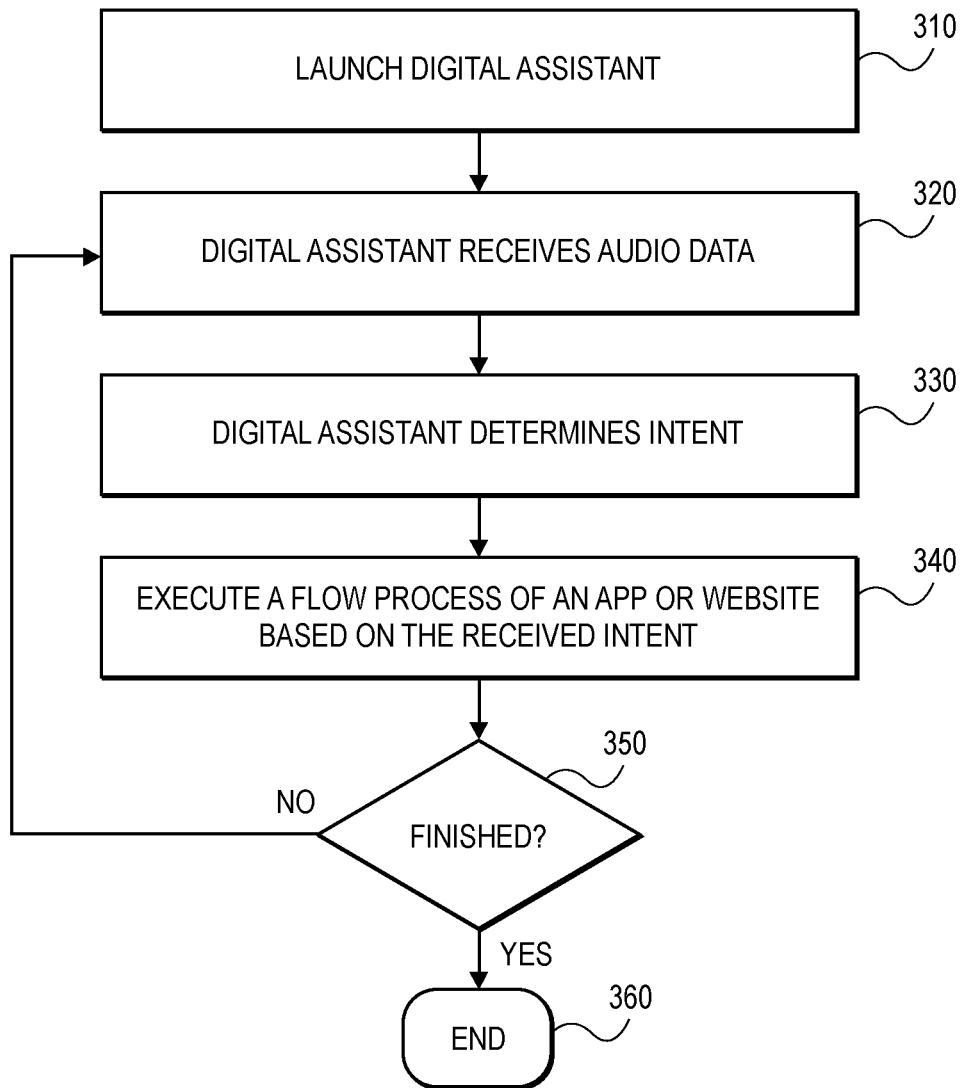
FIG. 3 shows a flowchart of an example implementation of a process, including an intent being determined by a digital assistant.

FIG. 3 shows an example implementation of a process including using a digital assistant. With reference thereto, at step 310, digital assistant 107 is launched on a mobile device, such as mobile device 111*m*. Although the example of FIG. 1 illustrates the digital assistant 107 running on the mobile device 111*m*, it should be understood that the digital assistant 107 may be run on any computing device, such as mobile device 113*m*, car 150, smart speaker 155, smart home 160, and so forth. At step 320, the digital assistant 107 receives the audio data (e.g., by the user speaking into the smartphone).

At step 330, the digital assistant 107 determines an intent of the user based on the received audio data. The digital assistant 107 determines the intent based on analyzing words, phrases, sounds, etc. from the audio data. At step 340, a flow (e.g., a flow process) of app 112 or of a website maintained by healthcare provider 101 is executed based on the determined intent. The flow process may be executed by linking or deep linking to a Uniform Resource Indicator (URI) or Uniform Resource Locator (URL). In some embodiments, this is accomplished by defining an Extensible Markup Language (XML) file within the app 112 to map the intent to the URI or URL. The flow may be any of the flows discussed herein.

To further illustrate, in one example of steps 330 and 340, if the user says, "Hey digital assistant, place order to refill prescription XYZ at pharmacy ABC," the digital assistant 107 may access a flow of a pharmacy app (e.g., app 112) to place the order for prescription. Moreover, it should be understood that in some embodiments, the app 112 does not have access to the audio data, and rather only has access to the determined intent. In this way, less information is shared, thereby improving data privacy and security.

At step 350, the digital assistant 107 determines if the user is finished using the digital assistant. If so, the method ends at step 360. If not, the method returns to step 320 and additional audio data is received.

Furthermore, although the example of FIG. 3 is illustrated with respect to audio data, it should be understood that any digital data, such as text message data, may be used in addition to or in place of the audio data.

Figure 4:
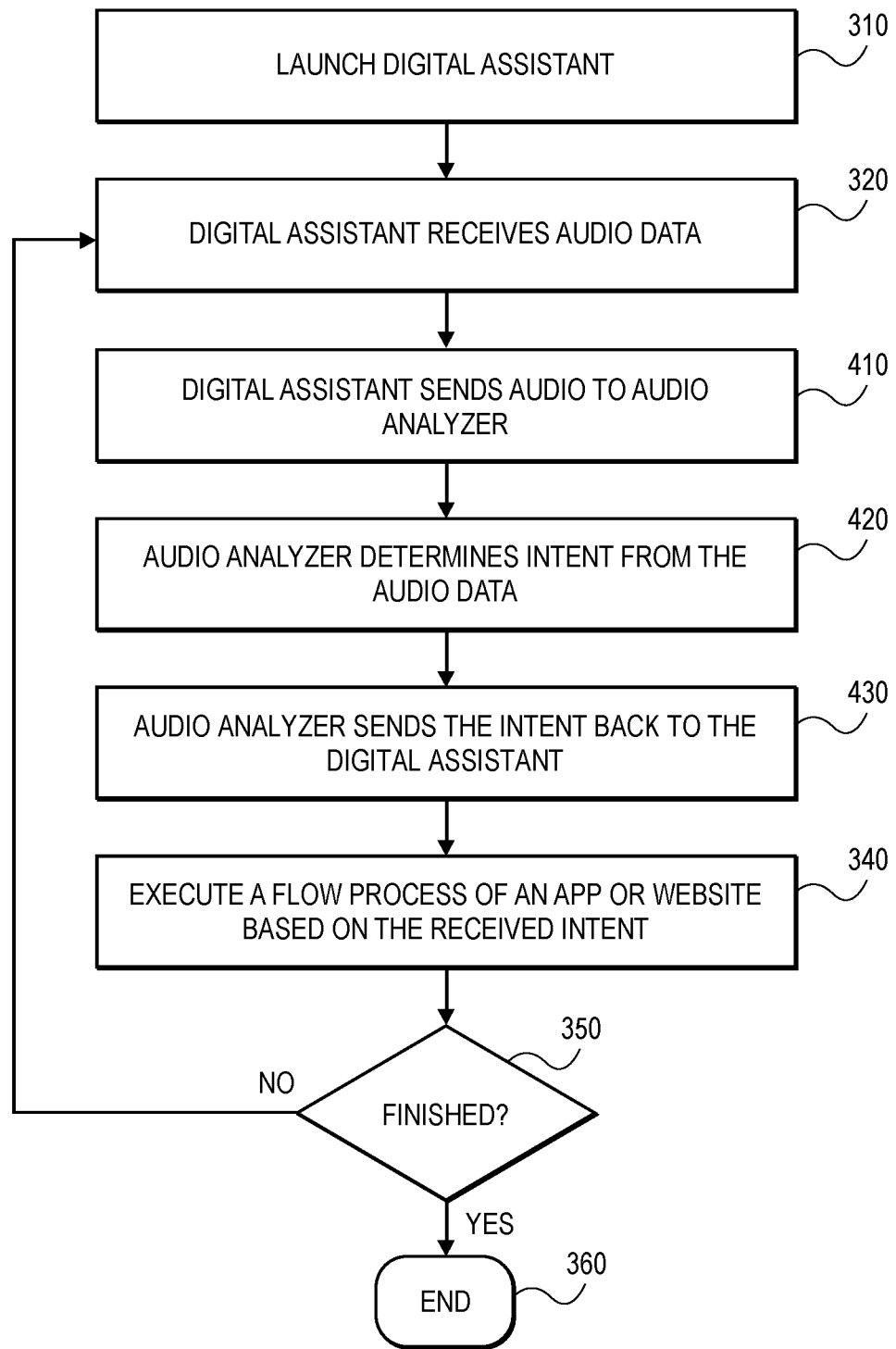
FIG. 4 shows an example implementation of a process, including audio data being sent to an audio analyzer to determine an intent.

FIG. 4 shows an example implementation of a process, including audio data being sent to an audio analyzer 130 to determine an intent. With reference thereto, at step 310, digital assistant 107 is launched on a mobile device 310, such as mobile device 111*m*. Although the example of FIG. 1 illustrates the digital assistant 107 running on the mobile device 111*m*, it should be understood that the digital assistant 107 may be run on any computing device, such as mobile device 113*m*, car 150, smart speaker 155, smart home 160, and so forth. At step 320, the digital assistant 107 receives the audio data (e.g., by the user speaking into the smartphone).

At step 410, the digital assistant 107 sends the audio data to the audio analyzer 130. At step 420, the audio analyzer 130 analyzes the audio data (e.g., using model 138) to determine an intent. The audio analyzer 130 may determine the intent based on analyzing words, phrases, sounds, etc. At step 430, the audio analyzer 130 sends the determined intent back to the digital assistant. In some embodiments, the audio analyzer 130 sends only the intent back to the digital assistant, and the audio analyzer 130 deletes the audio data so that no entity has a copy of the audio data, thereby improving data privacy and security.

At step 340, a flow process is executed (e.g., by the digital assistant 107, app 112, or website of the healthcare provider 101) based on the received intent. The flow process may be executed by linking or deep linking to a URI or URL. In some embodiments, this is accomplished by defining an XML file within the app 112 to map the intent to the URI or URL. The flow may be any of the flows discussed herein.

At step 350, the digital assistant 107 determines if the method is finished. If so, the method ends at step 360. If not, the method returns to step 320, and additional audio data is sent to the audio analyzer 130.

Furthermore, although the example of FIG. 4 is illustrated with respect to audio data, it should be understood that any digital data, such as text message data, may be used in addition to or in place of the audio data.

Additional Exemplary Embodiments

Aspect 1. In one aspect, there is computer computer-implemented method for voice assisted healthcare, the method comprising:

determining an intent from digital data, wherein the digital data comprises audio data or text message data;

matching the determined intent to a flow of a set of flows, wherein the set of flows includes at least one of: (i) submitting a prescription, (ii) refilling a prescription, (iii) changing a pickup location, (iv) requesting a status update for a prescription, or (v) initiating a pharmacy chat session; and executing the matched flow of the set of flows.

Aspect 2. The computer-implemented method of aspect 1, wherein the executing the flow of the set of flows comprises:

using an Extensible Markup Language (XML) file to access a Uniform Resource Identifier (URI).

Aspect 3. The computer-implemented method of any of aspects 1-2, wherein the executing the flow of the set of flows comprises:
deep linking to a Uniform Resource Locator (URL).

Aspect 4. The computer-implemented method of any of aspects 1-3, further comprising:
receiving, with a digital assistant of a mobile device, the digital data; and
wherein the matching the determined intent to a flow of the set of flows is done by the digital assistant of the mobile device.

Aspect 5. The computer-implemented method of any of aspects 1-4, further comprising:
receiving, with a digital assistant of a mobile device, the digital data; and
sending the digital data from the digital assistant to an audio analyzer;
wherein the matching the determined intent to a flow of the set of flows is done by the digital assistant of the mobile device; and
wherein the method further comprises sending the determined intent from the audio analyzer to the digital assistant.

Aspect 6. The computer-implemented method of any of aspects 1-5, wherein:
the intent is determined by a digital assistant that receives the digital data; and
the digital assistant sends only the determined intent to an app of a healthcare provider, and does not send the digital data to the app of the healthcare provider.

Aspect 7. The computer-implemented method of any of aspects 1-6, wherein:
the intent is determined by an audio analyzer that receives the digital data; and
the audio analyzer sends only the determined intent to a healthcare provider, and does not send the audio data to the healthcare provider.

Aspect 8. The computer-implemented method of any of aspects 1-7, wherein the set of flows includes all of: (i) submitting a prescription, (ii) refilling a prescription, (iii) changing a pickup location, (iv) requesting a status update for a prescription, and (v) initiating a pharmacy chat session.

Aspect 9. The computer-implemented method of any of aspects 1-8, wherein the intent is determined from words or phrases from the digital data.

Aspect 10. A computer computer-implemented method for voice assisted healthcare, the method comprising:
determining an intent from digital data, wherein the digital data comprises audio data or text message data;
matching the determined intent to a flow of a set of flows, wherein the set of flows includes locating at least one of: (i) a doctor's office, (ii) an online medical care provider, (iii) a site providing virus testing, (iv) a site administering a vaccine, (v) a provider of mental healthcare, (vi) a vision care provider, (vii) a hearing care provider or (viii) a physical therapist; and executing the matched flow of the set of flows.

Aspect 11. The computer-implemented method of aspect 10, wherein the executing the flow of the set of flows comprises:
using an Extensible Markup Language (XML) file to access a Uniform Resource Identifier (URI).

Aspect 12. The computer-implemented method of any of aspects 10-11, wherein the executing the flow of the set of flows comprises:
deep linking to a Uniform Resource Locator (URL).

Aspect 13. The computer-implemented method of any of aspects 10-12, further comprising:
receiving, with a digital assistant of a mobile device, the digital data;
wherein the matching the determined intent to a flow of the set of flows is done by the digital assistant of the mobile device.

Aspect 14. The computer-implemented method of any of aspects 10-13, further comprising:
receiving, with a digital assistant of a mobile device, the digital data; and
sending the digital data from the digital assistant to an audio analyzer;
wherein the matching the determined intent to a flow of the set of flows is done by the digital assistant of the mobile device; and
wherein the method further comprises sending the determined intent from the audio analyzer to the digital assistant.

Aspect 15. The computer-implemented method of any of aspects 10-14, wherein the set of flows includes locating all of: (i) a doctor's office, (ii) an online medical care provider, (iii) a site providing virus testing, (iv) a site administering a vaccine, (v) a provider of mental healthcare, (vi) a vision care provider, (vii) a hearing care provider, and (viii) a physical therapist.

Aspect 16. A computer system for voice assisted healthcare, the computer system comprising one or more processors configured to:
determine an intent from audio data;
match the determined intent to a flow of a set of flows, wherein the set of flows includes at least one of: (i) submitting a prescription, (ii) refilling a prescription, (iii) changing a pickup location, (iv) requesting a status update for a prescription, or (v) initiating a pharmacy chat session; and execute the matched flow of the set of flows.

Aspect 17. The computer system of aspect 16, wherein the one or more processors are further configured to execute the flow of the set of flows by:
using an Extensible Markup Language (XML) file to access a Uniform Resource Identifier (URI).

Aspect 18. The computer system of any of aspects 16-17, wherein the one or more processors are further configured to execute the flow of the set of flows by:
deep linking to a Uniform Resource Locator (URL).

Aspect 19. The computer system of any of aspects 16-18, wherein the one or more processors are further configured to:
receive, with a digital assistant of a mobile device, the audio data;
wherein the matching the determined intent to a flow of the set of flows is done by the digital assistant of the mobile device.

Aspect 20. The computer system of any of aspects 16-19, wherein the one or more processors are further configured to:
receive, with a digital assistant of a mobile device, the audio data;
send the audio data from the digital assistant to an audio analyzer; and
receive, with the digital assistant, an intent from the audio analyzer, wherein the intent was determined by the audio analyzer based on the audio data.

Other Matters

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor), such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of geographic locations.

What is claimed:

1. A computer-implemented method for voice assisted healthcare, the method comprising:
   determining an intent from digital data, wherein the digital data comprises audio data or text message data;
   matching the determined intent to a flow of a set of flows, wherein the set of flows includes at least one of: (i) submitting a prescription, (ii) refilling a prescription, (iii) changing a pickup location, (iv) requesting a status update for a prescription, or (v) initiating a pharmacy chat session; and
   executing the matched flow of the set of flows;
   wherein the intent is determined by a digital assistant that receives the digital data; and
   wherein the digital assistant sends only the determined intent to an app of a healthcare provider, and does not send the digital data to the app of the healthcare provider.

2. The computer-implemented method of claim 1, wherein the executing the flow of the set of flows comprises:
   using an Extensible Markup Language (XML) file to access a Uniform Resource Identifier (URI).

3. The computer-implemented method of claim 1, wherein the executing the flow of the set of flows comprises:
   deep linking to a Uniform Resource Locator (URL).

4. The computer-implemented method of claim 1, further comprising:
   receiving, with the digital assistant, the digital data; and
   wherein the matching the determined intent to a flow of the set of flows is done by the digital assistant.

5. The computer-implemented method of claim 1, wherein the set of flows includes all of: (i) submitting a prescription, (ii) refilling a prescription, (iii) changing a pickup location, (iv) requesting a status update for a prescription, and (v) initiating a pharmacy chat session.

6. The computer-implemented method of claim 1, wherein the intent is determined from words or phrases from the digital data.

7. The computer-implemented method of claim 1, wherein the set of flows includes at least two of: (i) submitting a prescription, (ii) refilling a prescription, (iii) changing a pickup location, (iv) requesting a status update for a prescription, and/or (v) initiating a pharmacy chat session.

8. A computer system for voice assisted healthcare, the computer system comprising one or more processors configured to:
   determine, via a digital assistant, an intent from digital data;
   match the determined intent to a flow of a set of flows, wherein the set of flows includes at least one of: (i) submitting a prescription, (ii) refilling a prescription, (iii) changing a pickup location, (iv) requesting a status update for a prescription, or (v) initiating a pharmacy chat session;

execute the matched flow of the set of flows; and send, via the digital assistant, only the determined intent to an app of a healthcare provider, and not send the digital data to the app of the healthcare provider.

9. The computer system of claim 8, wherein the one or more processors are further configured to execute the flow of the set of flows by:

using an Extensible Markup Language (XML) file to access a Uniform Resource Identifier (URI).

10. The computer system of claim 8, wherein the one or more processors are further configured to execute the flow of the set of flows by:

deep linking to a Uniform Resource Locator (URL).

11. The computer system of claim 8, wherein the one or more processors are further configured to:

receive, with the digital assistant, the digital data;

wherein the matching the determined intent to a flow of the set of flows is done by the digital assistant.

12. The computer system of claim 8, wherein the set of flows includes at least two of: (i) submitting a prescription, (ii) refilling a prescription, (iii) changing a pickup location, (iv) requesting a status update for a prescription, and/or (v) initiating a pharmacy chat session.

13. The computer system of claim 8, wherein the set of flows includes all of: (i) submitting a prescription, (ii) refilling a prescription, (iii) changing a pickup location, (iv) requesting a status update for a prescription, and (v) initiating a pharmacy chat session.

14. A computer-implemented method for voice assisted healthcare, the method comprising:

determining an intent from digital data, wherein the digital data comprises audio data or text message data;

matching the determined intent to a flow of a set of flows, wherein the set of flows includes at least one of: (i) submitting a prescription, (ii) refilling a prescription, (iii) changing a pickup location, (iv) requesting a status update for a prescription, or (v) initiating a pharmacy chat session; and executing the matched flow of the set of flows;

wherein the intent is determined by an audio analyzer that receives the digital data; and wherein the audio analyzer sends only the determined intent to a healthcare provider, and does not send the digital data to the healthcare provider.

15. The computer-implemented method of claim 14, wherein the executing the flow of the set of flows comprises:

using an Extensible Markup Language (XML) file to access a Uniform Resource Identifier (URI).

16. The computer-implemented method of claim 14, wherein the executing the flow of the set of flows comprises:

deep linking to a Uniform Resource Locator (URL).

17. The computer-implemented method of claim 14, wherein the intent is determined from words or phrases from the digital data.

18. The computer-implemented method of claim 14, wherein the set of flows includes at least two of: (i) submitting a prescription, (ii) refilling a prescription, (iii) changing a pickup location, (iv) requesting a status update for a prescription, and/or (v) initiating a pharmacy chat session.

19. The computer-implemented method of claim 14, wherein the set of flows includes all of: (i) submitting a prescription, (ii) refilling a prescription, (iii) changing a pickup location, (iv) requesting a status update for a prescription, and (v) initiating a pharmacy chat session.

\* \* \* \* \*